US012557973B2

(12) United States Patent (10) Patent No.: US 12,557,973 B2
Shimono (45) Date of Patent: Feb. 24, 2026

(54) OPTICAL UNIT, IMAGE PICKUP UNIT, AND ENDOSCOPE

(71) Applicant: OLYMPUS CORPORATION, Hachioji (JP)

(72) Inventor: Takahiro Shimono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 489 days.

(21) Appl. No.: 18/088,281

(22) Filed: Dec. 23, 2022

(65) Prior Publication Data

US 2023/0130026 A1 Apr. 27, 2023

Related U.S. Application Data

(63) Continuation of application No. PCT/JP2020/025590, filed on Jun. 29, 2020.

(51) Int. Cl.
*A61B 1/00* (2006.01)
*A61B 1/05* (2006.01)
(52) U.S. Cl.
CPC ...... *A61B 1/00188* (2013.01); *A61B 1/00096* (2013.01); *A61B 1/05* (2013.01)
(58) Field of Classification Search
CPC ... A61B 1/00188; A61B 1/00096; A61B 1/05; G02B 7/04; G02B 23/24
See application file for complete search history.

(56) References Cited

U.S. PATENT DOCUMENTS 5,212,595 A * 5/1993 Dennison, Jr. ........... G02B 7/04
359/823
5,409,748 A * 4/1995 Song ......................... C23C 4/02
165/177
(Continued)

FOREIGN PATENT DOCUMENTS

JP 5-12686 B2 2/1993
JP 7-168062 A 7/1995
(Continued)

OTHER PUBLICATIONS

International Search Report dated Sep. 24, 2020, issued in counterpart International Application No. PCT/JP2020/025590, with English Translation. (4 pages).

*Primary Examiner* — Anh Tuan T Nguyen
*Assistant Examiner* — Shankar Raj Ghimire
(74) *Attorney, Agent, or Firm* — WHDA, LLP

(57) ABSTRACT

An objective optical unit includes: an observation optical system including a fixed lens and a moving lens; a fixed barrel holding the fixed lens; a moving lens barrel disposed in a coil holding barrel, holding a movable group lens, and moving in a direction along a photographing optical axis of the observation optical system; a first film formed on slide surfaces of the coil holding barrel and the moving lens barrel, the first film serving as an oxidation reaction prevention layer; a second film interposed between the slide surface where the first film is formed and the first film, the second film serving as a stress reduction layer; and a voice coil motor configured to relatively move the moving lens barrel with respect to the fixed barrel in an optical axis direction by using a coil disposed at the fixed barrel and a magnet disposed at the moving lens barrel.

18 Claims, 12 Drawing Sheets

(56) References Cited

U.S. PATENT DOCUMENTS

| | | | | |
|---|---|---|---|---|
| 5,490,015 A * | 2/1996 | Umeyama | .............. | H02N 2/025 |
| | | | | 359/813 |
| 5,675,444 A * | 10/1997 | Ueyama | .................. | G02B 7/10 |
| | | | | 359/814 |
| 6,203,926 B1 * | 3/2001 | Ahmad | ................ | C23C 14/042 |
| | | | | 428/673 |
| 6,767,322 B1 * | 7/2004 | Futatsugi | .......... | A61B 1/00096 |
| | | | | 600/129 |
| 8,264,104 B2 * | 9/2012 | Schrader | ................. | G02B 7/08 |
| | | | | 310/12.24 |
| 9,901,243 B2 * | 2/2018 | Yajima | ................. | A61B 1/0661 |
| 10,244,932 B2 * | 4/2019 | Fujii | ................. | A61B 1/00188 |
| 10,653,301 B2 * | 5/2020 | Iguchi | ................. | A61B 1/0019 |
| 10,739,548 B2 * | 8/2020 | Iguchi | ..................... | G02B 7/08 |
| 10,863,892 B2 * | 12/2020 | Saito | ................. | A61B 1/00188 |
| 12,082,777 B2 * | 9/2024 | Nagamizu | ............. | H02K 41/02 |
| 2001/0018552 A1 * | 8/2001 | Akiba | ............... | A61B 1/00188 |
| | | | | 600/146 |
| 2002/0128539 A1 * | 9/2002 | Higuma | ............ | G02B 23/2453 |
| | | | | 600/162 |
| 2003/0056285 A1 * | 3/2003 | Pollastri | .............. | A61G 13/102 |
| | | | | 4/574.1 |
| 2010/0105980 A1 * | 4/2010 | Shimizu | ............ | A61B 1/00096 |
| | | | | 600/101 |
| 2013/0193778 A1 * | 8/2013 | Wieters | ............. | A61B 1/00133 |
| | | | | 310/12.04 |
| 2015/0223674 A1 * | 8/2015 | Wieters | ............... | A61B 1/0011 |
| | | | | 74/89 |
| 2015/0282692 A1 * | 10/2015 | Wieters | .............. | A61B 1/00183 |
| | | | | 604/95.05 |
| 2017/0159186 A1 * | 6/2017 | Burke | ................... | C23C 28/324 |
| 2017/0258303 A1 * | 9/2017 | Iguchi | ...................... | G02B 7/09 |
| 2017/0332894 A1 * | 11/2017 | Fujii | ................. | A61B 1/00188 |
| 2018/0081164 A1 * | 3/2018 | Ito | ...................... | A61B 1/00188 |
| 2018/0235436 A1 * | 8/2018 | Saito | ................. | A61B 1/00096 |
| 2018/0235450 A1 * | 8/2018 | Saito | ................. | A61B 1/00006 |
| 2018/0358722 A1 * | 12/2018 | Park | ................... | H05K 5/0069 |
| 2019/0082934 A1 * | 3/2019 | Matsunaga | ........ | A61B 1/00078 |
| 2020/0297192 A1 * | 9/2020 | Hanawa | ............. | A61B 1/00133 |
| 2021/0181457 A1 * | 6/2021 | Shimono | ................. | G02B 7/08 |
| 2021/0369088 A1 * | 12/2021 | Nagamizu | ......... | A61B 1/00188 |
| 2025/0016922 A1 * | 1/2025 | Shimizu | ................ | H04N 23/54 |

FOREIGN PATENT DOCUMENTS

| | | | |
|---|---|---|---|
| JP | 10-104494 A | | 4/1998 |
| JP | 2007-195658 A | | 8/2007 |
| JP | 2009-151273 A | | 7/2009 |
| JP | 2010-204242 A | | 9/2010 |
| JP | 2011-72907 A | | 4/2011 |
| JP | 5042656 B2 | | 10/2012 |
| JP | 2013-530672 A | | 7/2013 |
| JP | 2013-165886 A | | 8/2013 |
| JP | 2013-165892 A | | 8/2013 |
| JP | 2015-114651 A | | 6/2015 |
| JP | 5834074 B2 | | 12/2015 |
| JP | 2017-90504 A | | 5/2017 |
| WO | 2015/083490 A1 | | 6/2015 |
| WO | 2016/098225 A1 | | 6/2016 |

* cited by examiner

OPTICAL UNIT, IMAGE PICKUP UNIT, AND ENDOSCOPE

CROSS REFERENCE TO RELATED APPLICATION

This application is a continuation application of PCT/JP2020/025590 filed on Jun. 29, 2020, the entire contents of which are incorporated herein by this reference.

BACKGROUND OF THE INVENTION

1. Field of the Invention

The present invention relates to an optical unit in which a movable barrel can be moved in a direction along a photographing optical axis, an image pickup unit, and an endoscope.

2. Description of the Related Art

Conventionally, an endoscope has been disclosed and practically used. Such an endoscope includes, at a distal end portion, an optical unit, an optical property of which can be changed by a movable barrel (moving lens barrel) being moved forward and backward in an optical axis direction.

An optical unit of a voice coil motor (VCM) scheme has been known as an optical unit (observation optical unit) of such an endoscope, the optical unit including a fixed portion (fixed barrel) having a tubular shape, a movable barrel (movable portion) having a tubular shape and disposed inside the fixed barrel, a coil disposed at the fixed barrel, and a magnet disposed at the movable barrel.

In the optical unit of the VCM scheme, the movable barrel is driven at a high speed at autofocusing, for example. Thus, in the optical unit of the VCM scheme, surfaces of slide parts of the fixed barrel and the movable barrel oxidize (degrade), and furthermore, an infinitesimally small amount of corrosion powder is potentially generated from the oxidized surfaces.

After use or the like, an endoscope on which the optical unit of the VCM scheme is mounted is typically subjected to ultrasound clean in a state in which a coil of a VCM is tuned off (in other words, in a state in which the movable barrel is movable relative to the fixed barrel). When such ultrasound clean is performed, the surfaces of the slide parts of the fixed barrel and the movable barrel are affected by frictional stress and frictional heat due to high-speed vibration of ultrasound and degraded by chemical reaction, and furthermore, infinitesimally small amounts of corrosion powder and abrasion powder are potentially generated.

Such degradation of the surfaces of the slide parts and generation of corrosion powder and the like increase slide resistance of the movable barrel against the fixed barrel. To accurately drive the movable barrel even when such slide resistance increase has occurred, sizes of the magnet and the coil included in the voice coil motor need to be increased.

For example, Japanese Patent Application Laid-Open Publication No. 2009-151273 discloses a technology of forming a thin film part on the surfaces of the slide parts of the movable barrel and the fixed barrel, the thin film part being made of diamond-like carbon (DLC), which is hard and has a small friction coefficient.

SUMMARY OF THE INVENTION

An optical unit according to an aspect of the present invention includes: an observation optical system including a fixed lens and a moving lens; a fixed barrel holding the fixed lens; a movable barrel disposed in the fixed barrel, holding the moving lens, and configured to move in a direction along a photographing optical axis of the observation optical system a first film formed on at least one of slide surfaces of the fixed barrel and the movable barrel that slide relative to each other, the first film serving as an oxidation reaction prevention layer configured to prevent corrosion of the slide surface; a second film interposed between the slide surface on which the first film is formed and the first film, the second film serving as a stress reduction layer configured to prevent crack of the first film; and a voice coil motor configured to relatively move the movable barrel with respect to the fixed barrel in the optical axis direction by using a coil disposed at the fixed barrel and a magnet disposed at the movable barrel.

An image pickup unit according to an aspect of the present invention includes the optical unit, and an image pickup device unit disposed on the optical axis of the optical unit.

An endoscope according to an aspect of the present invention includes the optical unit at a distal end portion of an insertion portion that is inserted into a subject.

DETAILED DESCRIPTION OF THE PREFERRED EMBODIMENT

An embodiment of the present invention will be described below with reference to the accompanying drawings. The drawings relate to an embodiment of the present invention, and FIG. 1 is a schematic configuration diagram of an endoscope system.

Figure 1:
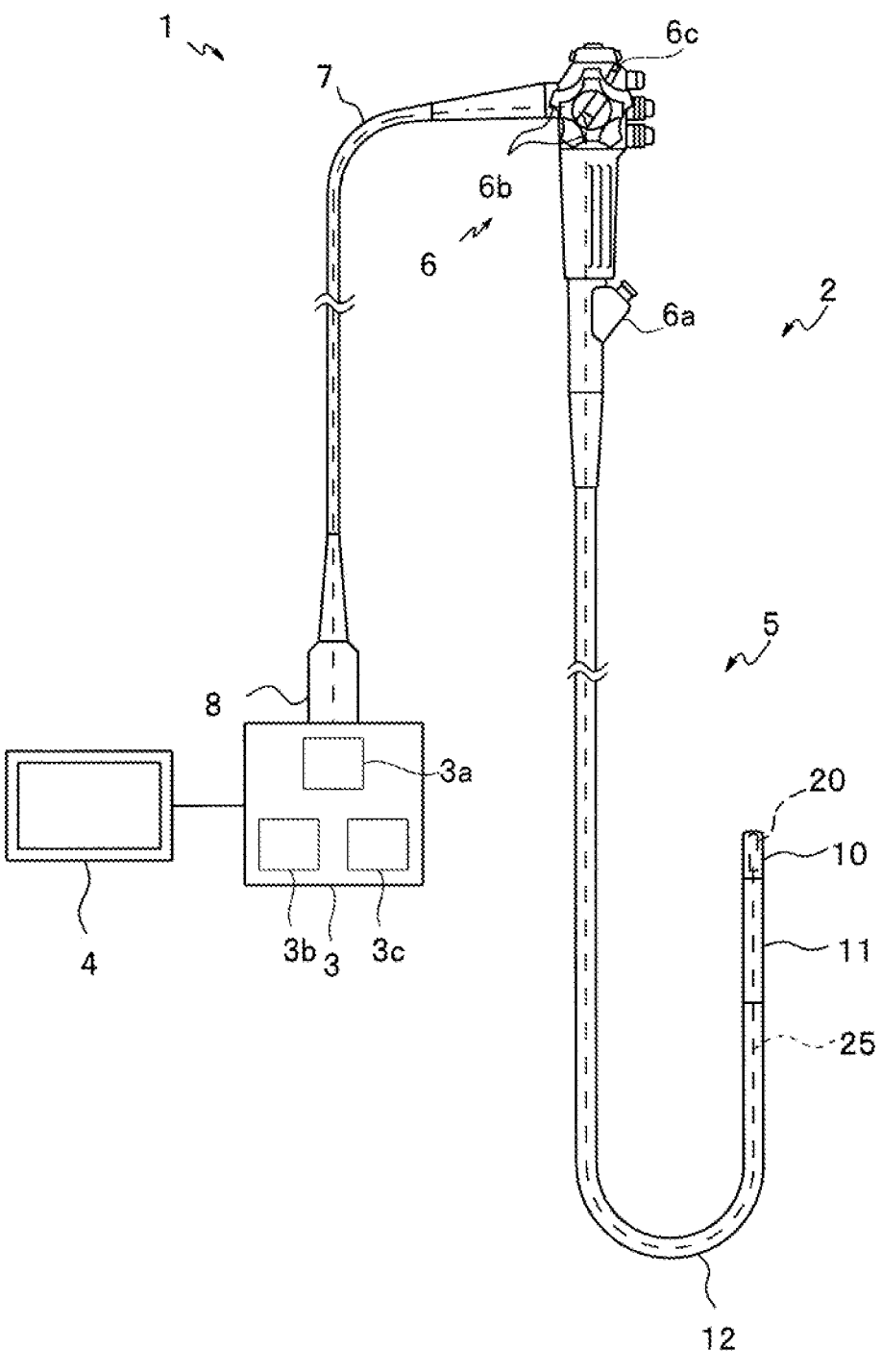
FIG. 1 is a schematic configuration diagram of an endoscope system.

An endoscope system 1 illustrated in FIG. 1 includes an endoscope 2, a control device 3, and a display device 4.

The endoscope 2 can be inserted into a subject such as a human body and is used to optically observe a predetermined observation site in the subject. Note that the subject into which the endoscope 2 is inserted is not limited to a human body but may be any other living body or may be an artifact such as a machine or a building.

The endoscope 2 includes an insertion portion 5 inserted into the subject, an operation portion 6 continuously provided on a proximal end side of the insertion portion 5, and a universal code 7 extended from the operation portion 6.

The insertion portion 5 includes, sequentially from a distal end side toward the proximal end side, a distal end portion 10, a bending portion 11 that is bendable, and a flexible tube portion 12.

Figure 2:
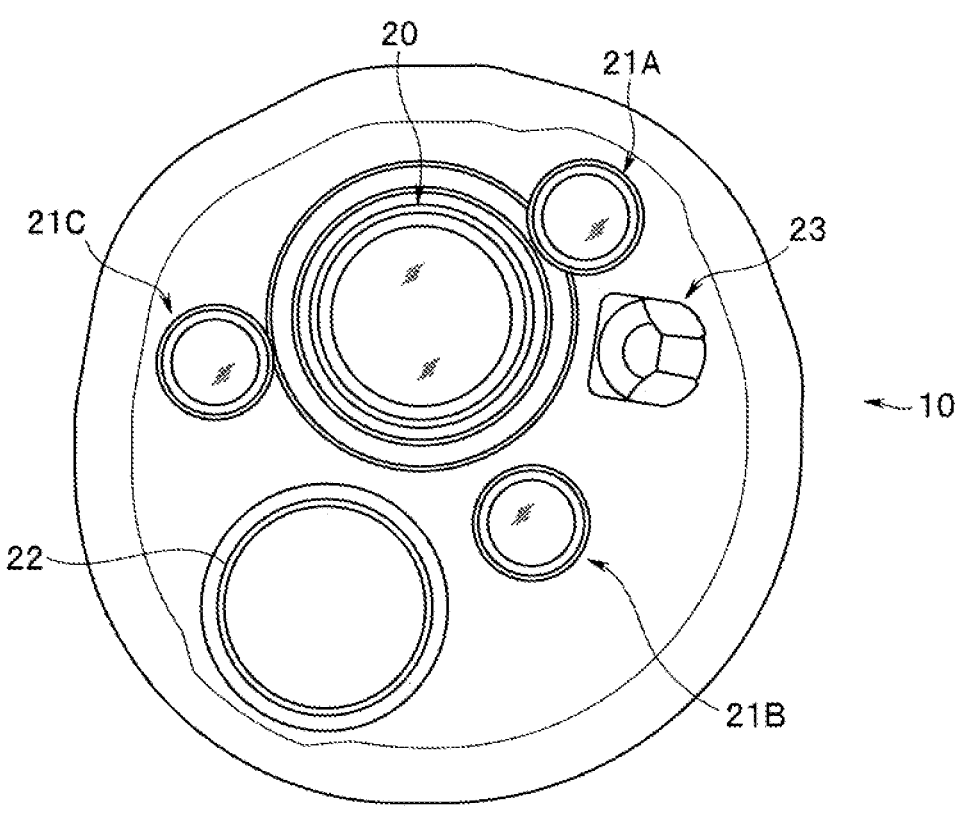
FIG. 2 is an end face diagram of a distal end portion.
Figure 3:
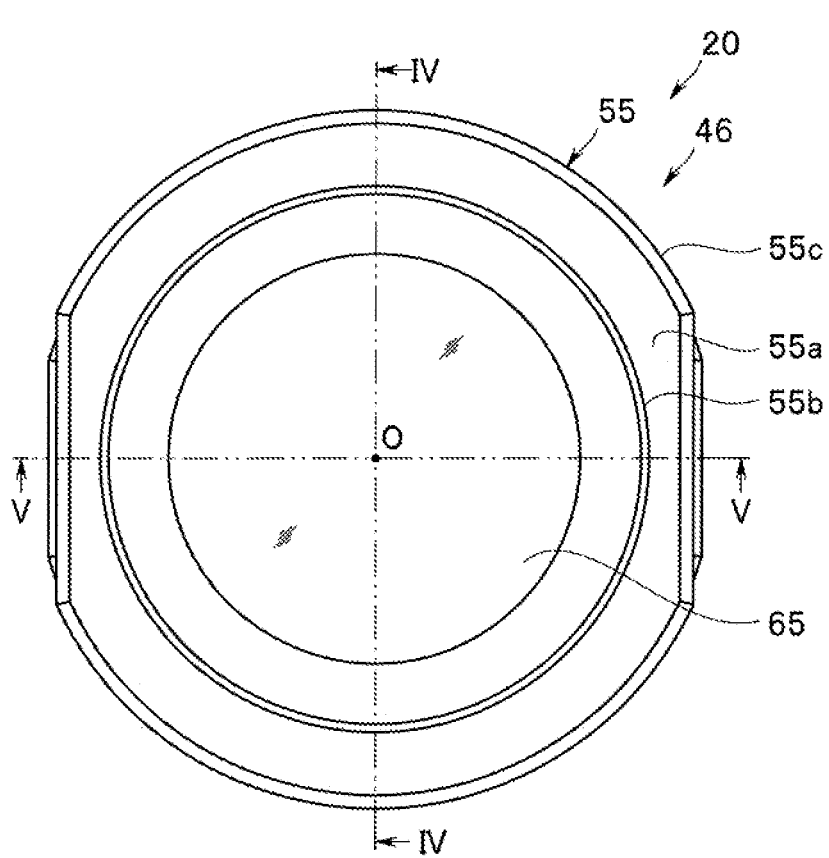
FIG. 3 is an end face diagram of an image pickup unit.
Figure 4:
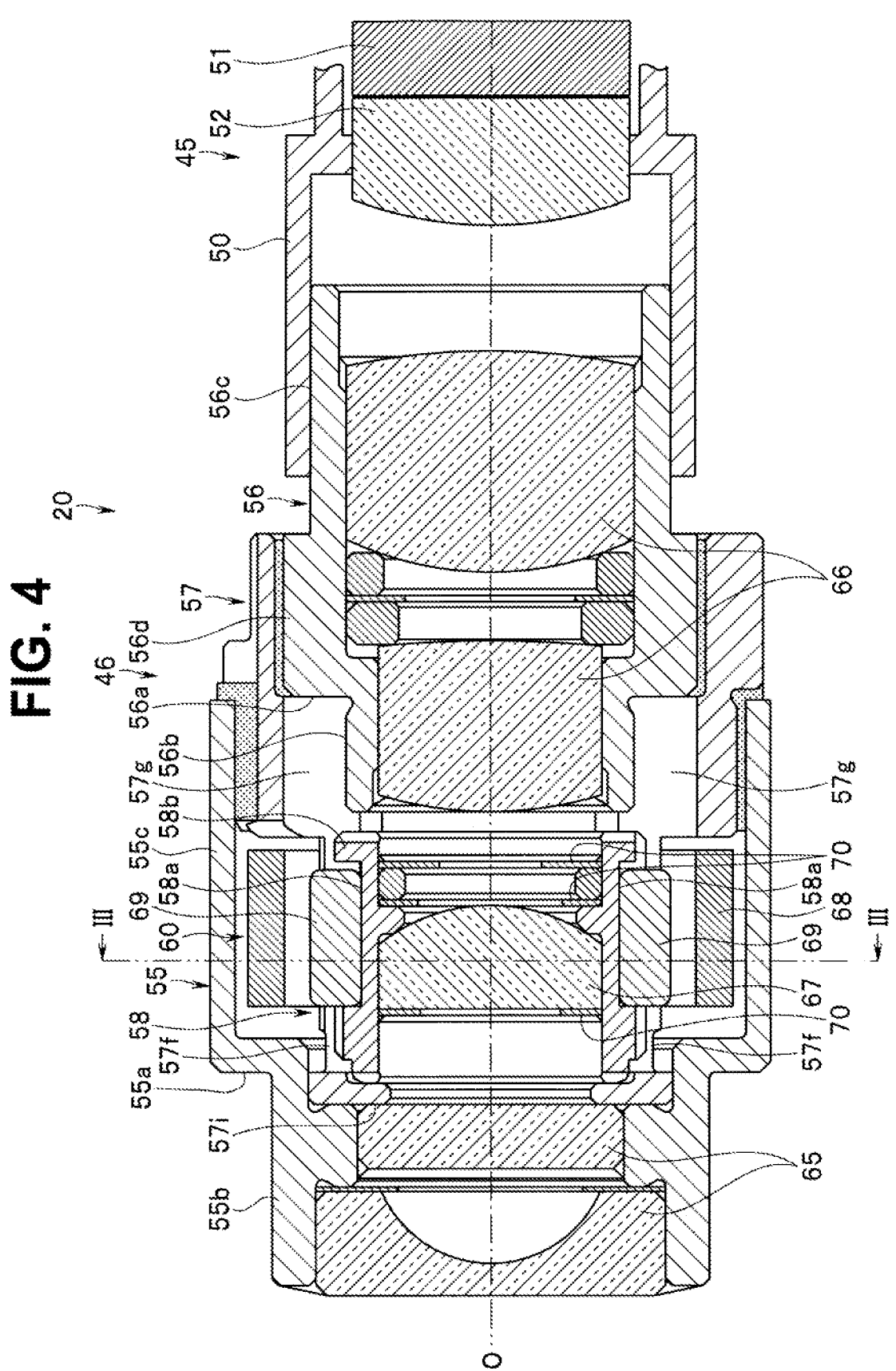
FIG. 4 is a IV-IV cross-sectional view of FIG. 3.
Figure 5:
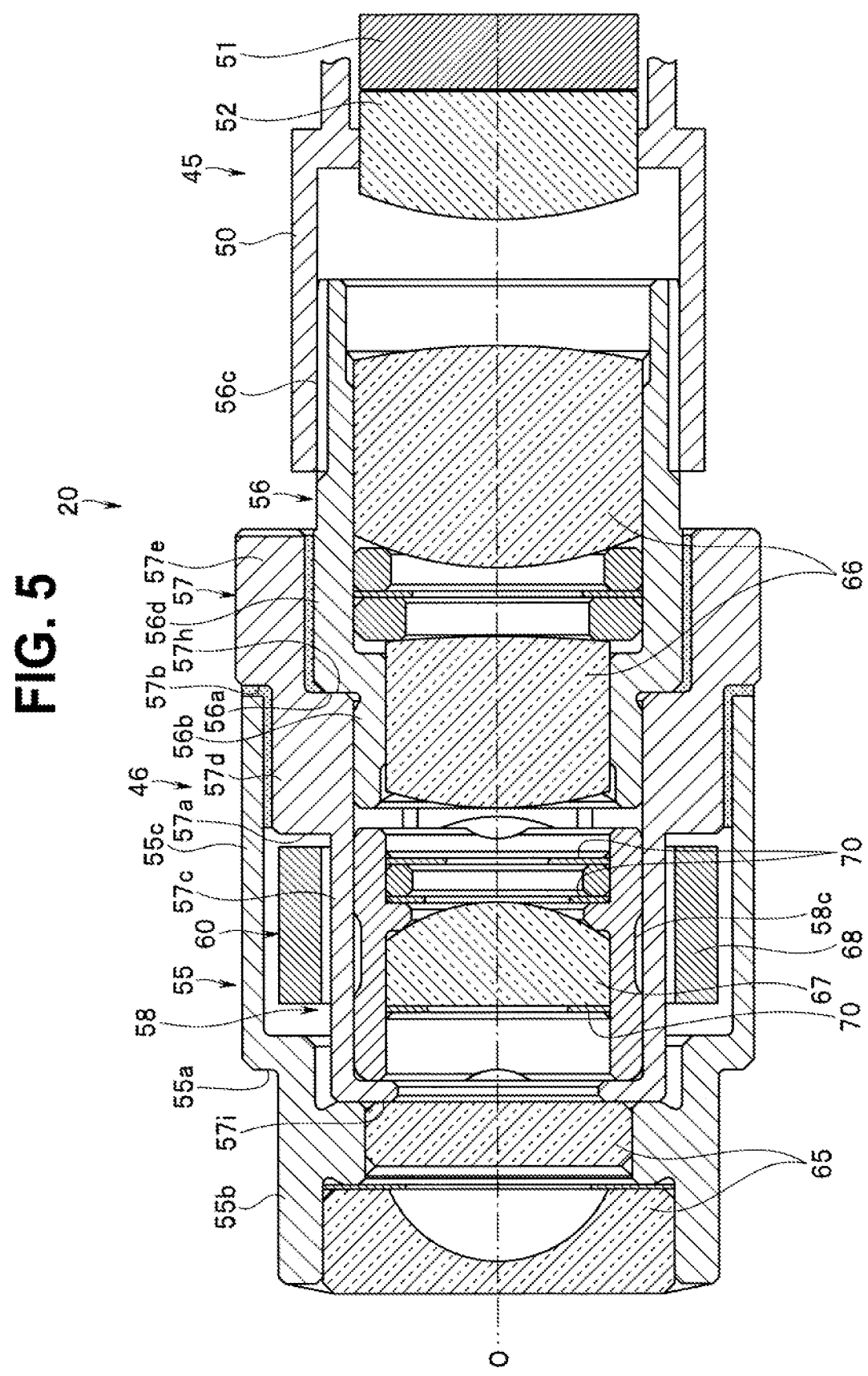
FIG. 5 is a V-V cross-sectional view of FIG. 3.
Figure 6:
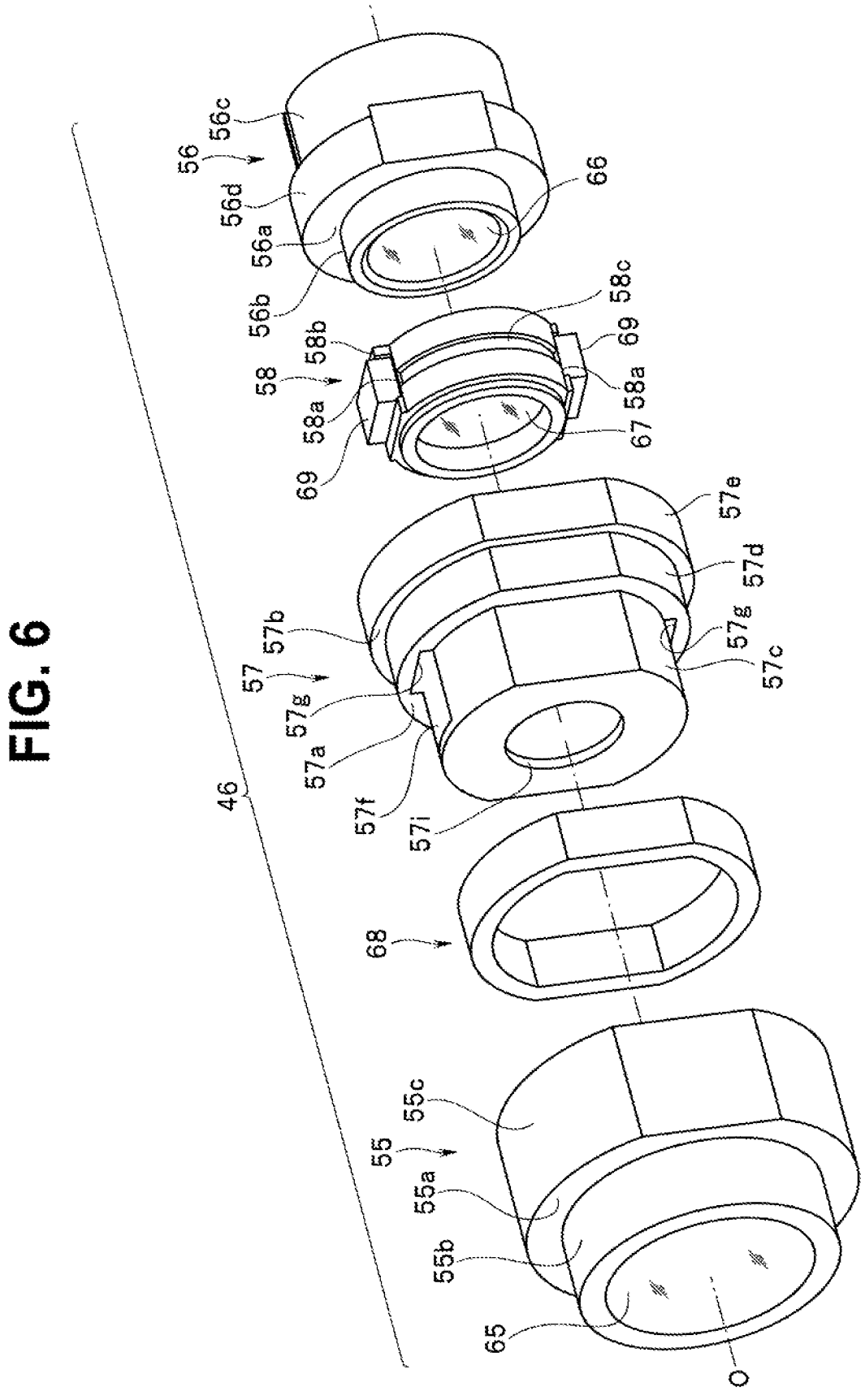
FIG. 6 is an exploded perspective view of an optical unit.

Although details will be described later, as illustrated in FIG. 2, the distal end portion 10 is provided with an image pickup unit 20 for forming a subject image on an image pickup device, a plurality of illumination optical system units (for example, three illumination optical system units: first to third illumination optical system units 21A to 21C), a treatment instrument channel port 22, and a gas-liquid feeding nozzle 23.

A composite cable 25 for performing transmission-reception of various signals (refer to FIG. 1) is connected to the image pickup unit 20.

Although not illustrated, first to third light guide bundles are connected to the first to third illumination optical system units 21A to 21C, respectively. A treatment instrument channel is connected to the treatment instrument channel port 22. A gas-liquid feeding tube is connected to the gas-liquid feeding nozzle 23.

The composite cable 25, the first to third light guide bundles, the treatment instrument channel, and the gas-liquid feeding tube are extended into the operation portion 6 through the bending portion 11 and the flexible tube portion 12. Note that the first to third light guide bundles are joined inside the flexible tube portion 12 and then extended as one light guide bundle into the operation portion 6.

The operation portion 6 is provided with a treatment instrument insertion port 6a as a proximal-end-side opening portion of the treatment instrument channel, an angle operation knob 6b for performing an operation to bend the bending portion 11, and a zoom lever 6c for performing an operation to change an optical property of the image pickup unit 20.

The composite cable 25, the light guide bundle, and the gas-liquid feeding tube extended into the operation portion 6 are inserted into the universal code 7. An endoscope connector 8 that is detachably connected to the control device 3 is provided at a proximal end portion of the universal code 7.

The endoscope connector 8 is configured to connect the composite cable 25, the light guide bundle, and the gas-liquid feeding tube to the control device 3.

The control device 3 includes a processor such as a central processing unit (CPU) and collectively controls the entire endoscope system 1. The control device 3 includes an image control unit 3a, a light source control unit 3b, and a gas-liquid feeding control unit 3c.

The image control unit 3a is electrically connected to the image pickup unit 20 and the operation portion 6 through the composite cable 25. The image control unit 3a receives an operation signal to the zoom lever 6c and controls an optical property of an objective optical unit (to be described later) provided at the image pickup unit 20. In addition, the image control unit 3a controls drive of the image pickup device (to be described later) of the image pickup unit 20 and converts an image pickup signal outputted from the image pickup unit 20 into an image signal. An image thus converted by the image control unit 3a is displayed on the display device 4 such as a monitor. In this manner, in the present embodiment, the control device 3 including the image control unit 3a achieves functions of an image processing apparatus.

The light source control unit 3b is connected to a non-illustrated light source device built in the control device 3. The light source control unit 3b controls drive of the light source device, thereby controlling brightness and the like of illumination light supplied to the first to third illumination optical system units 21A to 21C through the light guide bundle (first to third light guide bundles).

The gas-liquid feeding control unit 3c is connected to a non-illustrated gas-liquid feeding device built in the control device 3. The gas-liquid feeding control unit 3c controls drive of the gas-liquid feeding device, thereby performing gas feeding or liquid feeding to the gas-liquid feeding nozzle 23 through the gas-liquid feeding tube.

Subsequently, a configuration of the image pickup unit 20 provided at the distal end portion 10 of the endoscope 2 will be specifically described with reference to FIGS. 3 to 7.

The image pickup unit 20 includes an image pickup device unit 45 and an objective optical unit 46 as an optical unit continuously provided on the distal end side of the image pickup device unit 45.

The image pickup device unit 45 includes an image pickup device holding barrel 50. An optical member 52 constituted by, for example, a lens formed flat on a back surface side is held at the image pickup device holding barrel 50. A front surface side of an image pickup device 51 constituted by a CCD, a CMOS, or the like is held on a back surface of the optical member 52 by a bonding agent or the like. An image pickup device substrate (not illustrated) on which various kinds of control circuits and the like are mounted is electrically connected on a back surface side of the image pickup device 51. Note that although not illustrated, various cables bifurcated from the composite cable 25 are electrically connected to the image pickup device substrate.

The objective optical unit 46 includes a front group lens barrel 55, a rear group lens barrel 56, and a coil holding barrel 57, which constitute a fixed barrel, and also includes a moving lens barrel 58 as a movable barrel that is slidably disposed inside the fixed barrel (the coil holding barrel 57). A voice coil motor 60 is built in the objective optical unit 46. The objective optical unit 46 can change an optical property of an observation optical system by moving the moving lens barrel 58 forward and backward in a direction of an optical axis O (photographing optical axis) by using the voice coil motor 60.

The front group lens barrel 55 is formed as a frame body having a substantially cylindrical shape. The front group lens barrel 55 is formed such that an outer diameter on the proximal end side is larger than an outer diameter on the distal end side. Since the outer diameters of the distal end side and the proximal end side are different from each other, a stepped part 55a is formed at an intermediate position on an outer peripheral surface of the front group lens barrel 55. The stepped part 55a is set as a contact surface for performing positioning in the direction of the optical axis O when the objective optical unit 46 is fixed to the distal end portion 10.

In the front group lens barrel 55, a front group lens 65 consisting of a plurality of fixed lenses is held inside a distal-end-side barrel part 55b positioned on the distal end side of the stepped part 55a. The front group lens 65 is included in the observation optical system of the objective optical unit 46.

In the front group lens barrel 55, a proximal-end-side barrel part 55c positioned on the proximal end side of the stepped part 55a is formed as an exterior member for covering the coil holding barrel 57.

The rear group lens barrel 56 is formed as a frame body having a substantially cylindrical shape. The rear group lens barrel 56 is formed larger on the proximal end side than on the distal end side. Since outer diameters of the distal end side and the proximal end side are different from each other, a stepped part 56a is formed at an intermediate position on an outer peripheral surface of the rear group lens barrel 56. The stepped part 56a is set as a contact surface for performing positioning relative to the coil holding barrel 57 in the direction of the optical axis O.

In the rear group lens barrel 56, an outer peripheral surface of a distal-end-side barrel part 56b positioned on the distal end side of the stepped part 56a is set as a fitting surface for fitting to the coil holding barrel 57.

In the rear group lens barrel 56, an outward flange 56d is provided at a proximal-end-side barrel part 56c positioned on the proximal end side of the stepped part 56a. A part of the outward flange 56d on the proximal end side of the proximal-end-side barrel part 56c is set as a fitting portion for externally fitting the image pickup device holding barrel 50.

A rear group lens 66 consisting of a plurality of fixed lenses is held inside the rear group lens barrel 56 (inside the distal-end-side barrel part 56b and the proximal-end-side barrel part 56c). The rear group lens 66 is included in the observation optical system of the objective optical unit 46.

The coil holding barrel 57 is formed as a frame body having a substantially cylindrical shape and disposed between the front group lens barrel 55 and the rear group lens barrel 56. The coil holding barrel 57 is formed such that an outer diameter at an intermediate position is larger than an outer diameter on the distal end side and an outer diameter on the proximal end side is larger than the outer diameter at the intermediate position. Since the outer diameter on the distal end side, the outer diameter at the intermediate position, and the outer diameter on the proximal end side are different from one another, a first stepped part 57a and a second stepped part 57b are formed on an outer peripheral surface of the coil holding barrel 57.

In the coil holding barrel 57, a volume reduction part 57f as a cutout part extending in the direction of the optical axis O is formed at each rotational position of 180° about the optical axis O at a distal-end-side barrel part 57c positioned on the distal end side of the first stepped part 57a. Note that an inward flange 57i for restricting movement of the moving lens barrel 58 toward the distal end side, which will be described later, is formed at a distal end of the distal-end-side barrel part 57c.

An annular coil 68 included in the voice coil motor 60 is disposed on an outer peripheral surface of the distal-end-side barrel part 57c. Two or more coils included in the voice coil motor 60 may be disposed alongside in the direction of the optical axis O on the distal-end-side barrel part 57c, but in the present embodiment, the only one coil 68 is disposed for downsizing of the objective optical unit 46.

In the coil holding barrel 57, an inner diameter of an intermediate barrel part 57d positioned between the first stepped part 57a and the second stepped part 57b is set to be equal to an inner diameter of the distal-end-side barrel part 57c. Groove parts 57g as cutout parts that are continuous with the respective volume reduction parts 57f are provided inside the intermediate barrel part 57d.

In the coil holding barrel 57, an inner diameter of a proximal-end-side barrel part 57e positioned on the proximal end side of the second stepped part 57b is set to be larger than the distal-end-side barrel part 57c and the intermediate barrel part 57d. Accordingly, a stepped part 57h is formed at a distal end inside the proximal-end-side barrel part 57e. Proximal end sides of the groove parts 57g are opened inside the proximal-end-side barrel part 57e.

The moving lens barrel 58 is formed as a frame body having a substantially cylindrical shape and having an outer diameter substantially equal to the inner diameters of the distal-end-side barrel part 57c and the intermediate barrel part 57d of the coil holding barrel 57. A flat surface 58a is formed at each rotational position of 180° on an outer peripheral surface of the moving lens barrel 58. Magnets 69 included in the voice coil motor 60 are held on the respective flat surfaces 58a.

The magnets 69 are disposed as protrusions from the respective flat surfaces 58a in an outer radial direction of the moving lens barrel 58. The magnets 69 are magnetized with polarity in a thickness direction (in other words, the outer radial direction of the moving lens barrel 58). Each magnet 69 in the present embodiment is disposed on the corresponding flat surface 58a and fixed by a bonding agent or the like, for example, with a south pole on an outer side in a radial direction of the moving lens barrel 58 and with a north pole on an inner side in the radial direction of the moving lens barrel 58.

A key 58b for engagement with a volume reduction part 57f and a groove part 57g of the coil holding barrel 57 is provided on at least one of the two flat surfaces 58a.

A groove part 58c as a recessed part having a circular are shape is provided on the outer peripheral surface of the moving lens barrel 58.

A movable group lens 67 consisting of one lens or two or more lenses is held inside the moving lens barrel 58. The movable group lens 67 is included in the observation optical system of the objective optical unit 46.

The moving lens barrel 58 thus configured is inserted inside the coil holding barrel 57. In this state, the magnets 69 are inserted into the volume reduction parts 57f through the groove parts 57g, respectively. Accordingly, the magnets 69 are positioned opposite to each other inside the coil 68. In addition, the key 58b is inserted into one of the volume reduction parts 57f through the corresponding groove part 57g. Accordingly, the key 58b is disposed in a manner engageable with the volume reduction part 57f and the groove part 57g and restricts rotation of the moving lens barrel 58 about the optical axis O. In other words, rotation of the moving lens barrel 58 about the optical axis O is restricted by the key 58b, and the moving lens barrel 58 is housed inside the coil holding barrel 57 in a state of being movable in the direction of the optical axis O.

The rear group lens barrel 56 is coupled on the proximal end side of the coil holding barrel 57 in which the moving lens barrel 58 is housed. Specifically, the rear group lens barrel 56 is connected in a state in which positioning is made with respect to the coil holding barrel 57 as the distal-end-side barrel part 56b is internally fitted to the intermediate barrel part 57d of the coil holding barrel 57 and the stepped part 56a contacts the stepped part 57h of the coil holding barrel 57. Then, a bonding agent is provided and cured between the outward flange 56d and the proximal-end-side barrel part 57e, and accordingly, the rear group lens barrel 56 is coupled to the coil holding barrel 57.

The front group lens barrel 55 is coupled on the distal end side of the coil holding barrel 57. Specifically, the front group lens barrel 55 is connected to the coil holding barrel 57 as the intermediate barrel part 57d of the coil holding barrel 57 is inserted into the proximal-end-side barrel part 55c. Then, a bonding agent is provided and cured between the intermediate barrel part 57d and the proximal-end-side barrel part 55c, and accordingly, the front group lens barrel 55 is coupled to the coil holding barrel 57.

Figure 7:
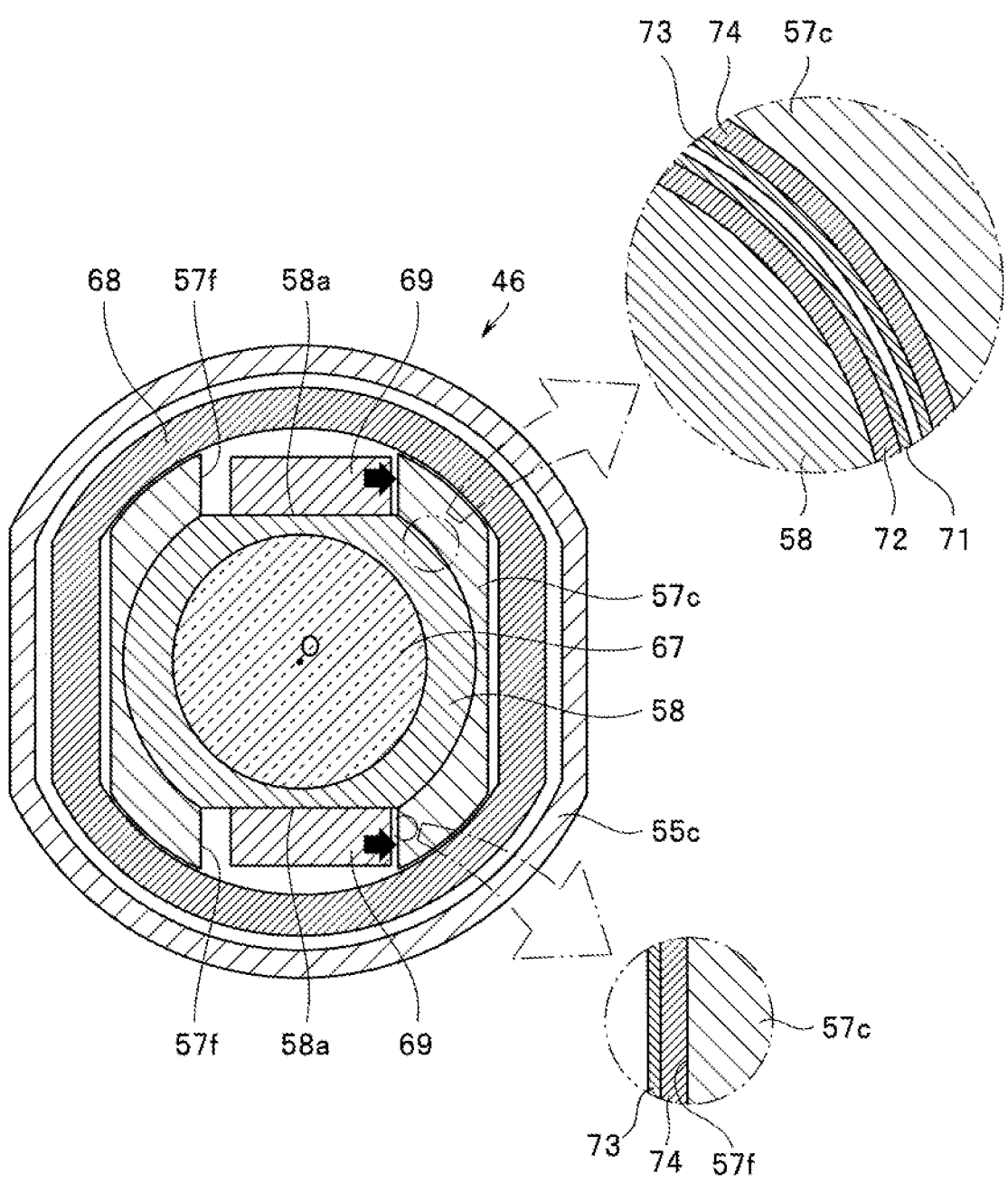
FIG. 7 is a VII-VII cross-sectional view of FIG. 4.

As illustrated in, for example, FIG. 7, to prevent increase of slide resistance of the moving lens barrel 58 in the objective optical unit 46 of the present embodiment, a first film 71 is formed on an outer peripheral surface of the moving lens barrel 58, which is a slide surface for the coil holding barrel 57, the first film 71 being an oxidize prevent layer for preventing oxidation (corrosion) of the outer peripheral surface. The first film 71 preferably contains a noble metal component. More specifically, the first film 71 preferably contains a component of any of gold, palladium, and platinum, which has a high corrosion resistance.

A second film 72 is formed between the outer peripheral surface of the moving lens barrel 58 as the slide surface for the coil holding barrel 57 and the first film 71, the second film 72 serving as a stress reduction layer for preventing crack of the first film 71. The second film 72 is preferably made of a material having a substantially same Young's modulus as the moving lens barrel 58. Moreover, the second film 72 is preferably made of a material having a substantially same linear expansion coefficient as a material of the first film 71. More specifically, the second film 72 is preferably made of a material containing a nickel (Ni) component. In addition, the second film 72 is preferably thicker than the first film 71. More specifically, the second film 72 is preferably at least twice thicker than the first film 71.

Similarly, a first film 73 is formed on an inner peripheral surface of the coil holding barrel 57, which is a slide surface for the moving lens barrel 58 (inner peripheral surfaces of the distal-end-side barrel part 57c and the intermediate barrel part 57d), the first film 73 being an oxidation prevention film for preventing oxidation (corrosion) of the inner peripheral surface. The first film 73 preferably contains a noble metal component. More specifically, the first film 73 preferably contains a component of any of gold, palladium, and platinum, which has a high corrosion resistance.

A second film 74 is formed between the inner peripheral surface of the coil holding barrel 57 as the slide surface for the moving lens barrel 58 and the first film 73, the second film 74 serving as a stress reduction layer for preventing crack of the first film 73. The second film 74 is preferably made of a material having a substantially same Young's modulus as the coil holding barrel 57. The second film 74 is preferably made of a material having a substantially same linear expansion coefficient as a material of the first film 73. More specifically, the second film 74 is preferably made of a material containing a nickel (Ni) component. In addition, the second film 74 is preferably thicker than the first film 73. More specifically, the second film 74 is preferably at least twice thicker than the first film 73.

The first film 73 and the second film 74 (or only the second film 74) formed on the slide surface of the coil holding barrel 57 are extended to the volume reduction parts 57f and the groove parts 57g. In this configuration in which at least the second film 74 containing a magnetic material such as nickel is extended to the volume reduction parts 57f and the groove parts 57g, the magnets 69 held on the respective flat surfaces 58a of the moving lens barrel 58 are offset in the same direction (for example, right direction on the sheet of FIG. 7) with respect to the optical axis O as illustrated in, for example. FIG. 7. Accordingly, the magnets 69 are attracted in the same direction to the coil holding barrel 57, thereby reducing backlash of the moving lens barrel 58 (refer to arrows in FIG. 7).

In the objective optical unit 46 assembled as described above, a distal end side of the image pickup device holding barrel 50 is coupled to a proximal end side of the rear group lens barrel 56. Accordingly, a subject image is formed on the image pickup device 51 through the observation optical system of the objective optical unit 46.

In the endoscope system 1 in which such an image pickup unit 20 is provided at the distal end portion 10 of the endoscope 2, when the zoom lever 6c is operated by a user or the like, the image control unit 3a of the control device 3 performs energization control on the coil 68 in accordance with a state of the operation on the zoom lever 6c. The magnets 69 being affected by a magnetic field generated at the coil 68 by the energization control move the moving lens barrel 58 in the direction of the optical axis O.

Since the moving lens barrel 58 in the direction of the optical axis O is moved at high speed, frictional stress and frictional heat occur to the slide surface of the moving lens barrel 58 for the coil holding barrel 57 and the slide surface of the coil holding barrel 57 for the moving lens barrel 58, but oxidation (degradation) of the slide surfaces due to the frictional stress and the frictional heat is prevented by the first films 71 and 73 as oxidation reaction prevention layers. In this case, since the first films 71 and 73 are made of a material such as gold and not as hard as diamond-like carbon and the like, crack is unlikely to occur and functions of the oxidation reaction prevention layers are maintained for a long time.

Moreover, since the second films 72 and 74 are each formed between the slide surface of the moving lens barrel 58 or the coil holding barrel 57 and the first film 71 or 73, damage on the first films 71 and 73 is more effectively prevented. Specifically, the first films 71 and 73 are each formed by, for example, what is called electroless gold plating in which the second film 72 or 74 of several μm, which is made of a nickel layer or the like, is provided as a base material. Accordingly, the second films 72 and 74 serve as buffers and reduce stress transferred onto the first films 71 and 73 even at high-speed movement of the moving lens barrel 58, ultrasound clean of the endoscope 2, or the like. Thus, occurrence of crack and the like to the first films 71 and 73 is more effectively prevented.

In this case, for example, detachment of the second films 72 and 74 (and the first films 71 and 73) from the moving lens barrel 58 and the coil holding barrel 57 is prevented by forming the second films 72 and 74 by using a material (for example, nickel) having a substantially same Young's modulus as a material (for example, SUS303) of the moving lens barrel 58 and the coil holding barrel 57.

In addition, for example, detachment of the first films 71 and 73 from the second films 72 and 74 (and the moving lens barrel 58 and the coil holding barrel 57) is prevented by forming the second films 72 and 74 by using a material (for example, nickel) having a substantially same linear expansion coefficient as the material (for example, gold) of the first films 71 and 73.

Moreover, the moving lens barrel 58 is provided with the groove part 58c on the outer peripheral surface, and thus when an infinitesimally small amount of powder dust such as abrasion powder is generated, the generated abrasion powder and the like can be collected by the groove part 58c and slide resistance increase due to generation of abrasion powder and the like is reduced.

As described above, according to the present embodiment, since slide resistance increase is reduced, it is possible to drive the moving lens barrel 58 with small drive power and minimize the number of components such as the coil 68 and the magnets 69 to achieve downsizing of the voice coil motor 60. Thus, it is possible to prevent slide resistance increase and achieve both operation performance and downsizing of the moving lens barrel 58.

In the present embodiment, as illustrated in, for example, FIG. 7, widths of the volume reduction parts 57*f* (and the groove parts 57*g*) are set to be sufficiently larger than widths of the magnets 69. With such a configuration, spaces on the distal end side and the proximal end side of the moving lens barrel 58 inside the coil holding barrel 57 are not blocked airtight but communicated. With the communication, the moving lens barrel 58 is prevented from acting as a piston that compresses or expands air in the spaces when the moving lens barrel 58 moves in the direction of the optical axis O inside the coil holding barrel 57. Thus, it is possible to reduce air resistance when the moving lens barrel 58 moves, and more efficiently achieve both operation performance and downsizing of the moving lens barrel 58.

Figure 8:
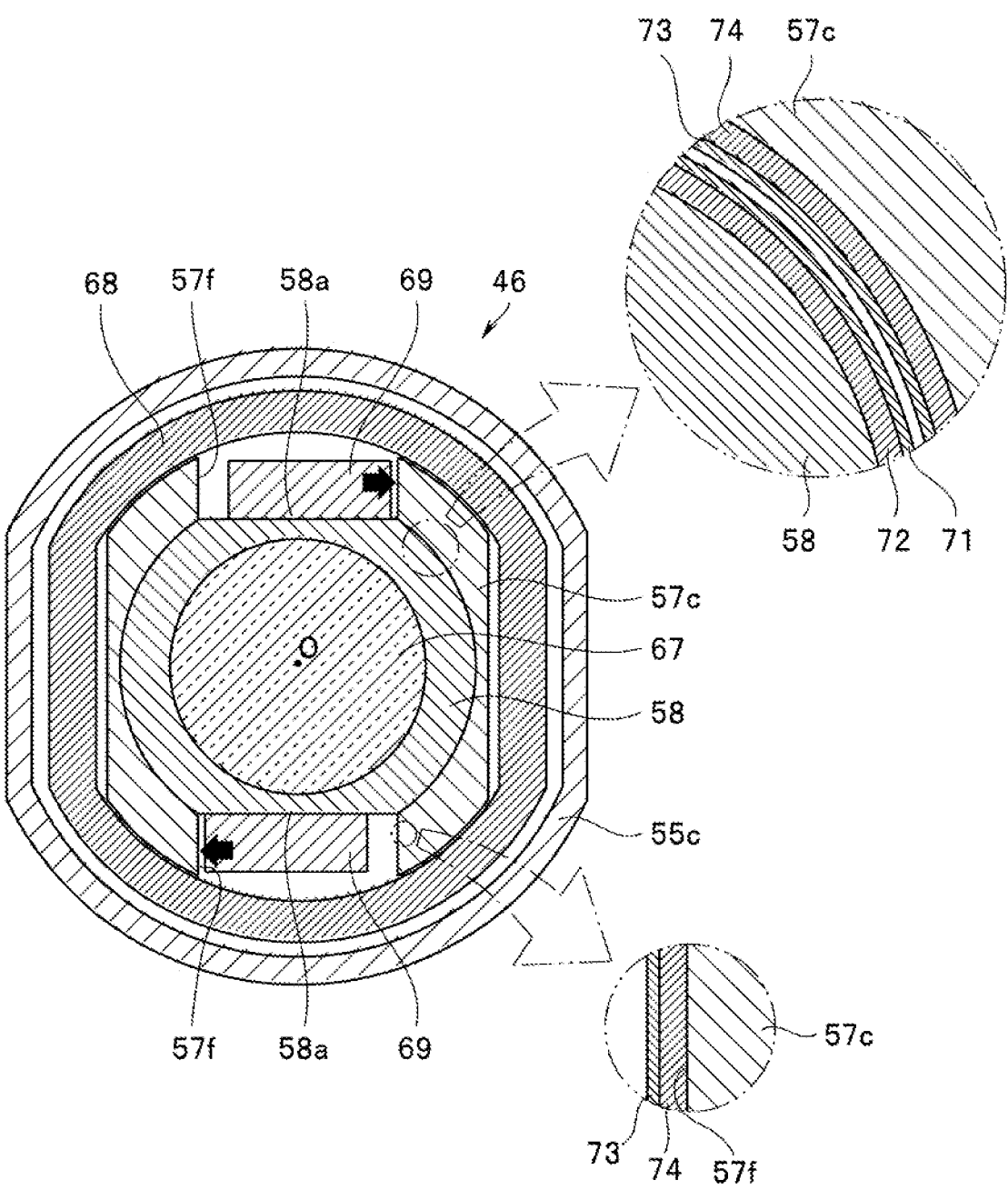
FIG. 8 relates to a first modification and is a cross-sectional view of an optical unit.

In the above-described embodiment, disposition of the magnets 69 on the respective flat surface 58*a* of the moving lens barrel 58 may be set to positions rotationally symmetric with respect to the optical axis O as illustrated in, for example, FIG. 8. With this configuration, the magnets 69 are attracted to the coil holding barrel 57 in a rotational direction centered at the optical axis O, thereby reducing backlash of the moving lens barrel 58 (refer to arrows in FIG. 8).

Figure 9:
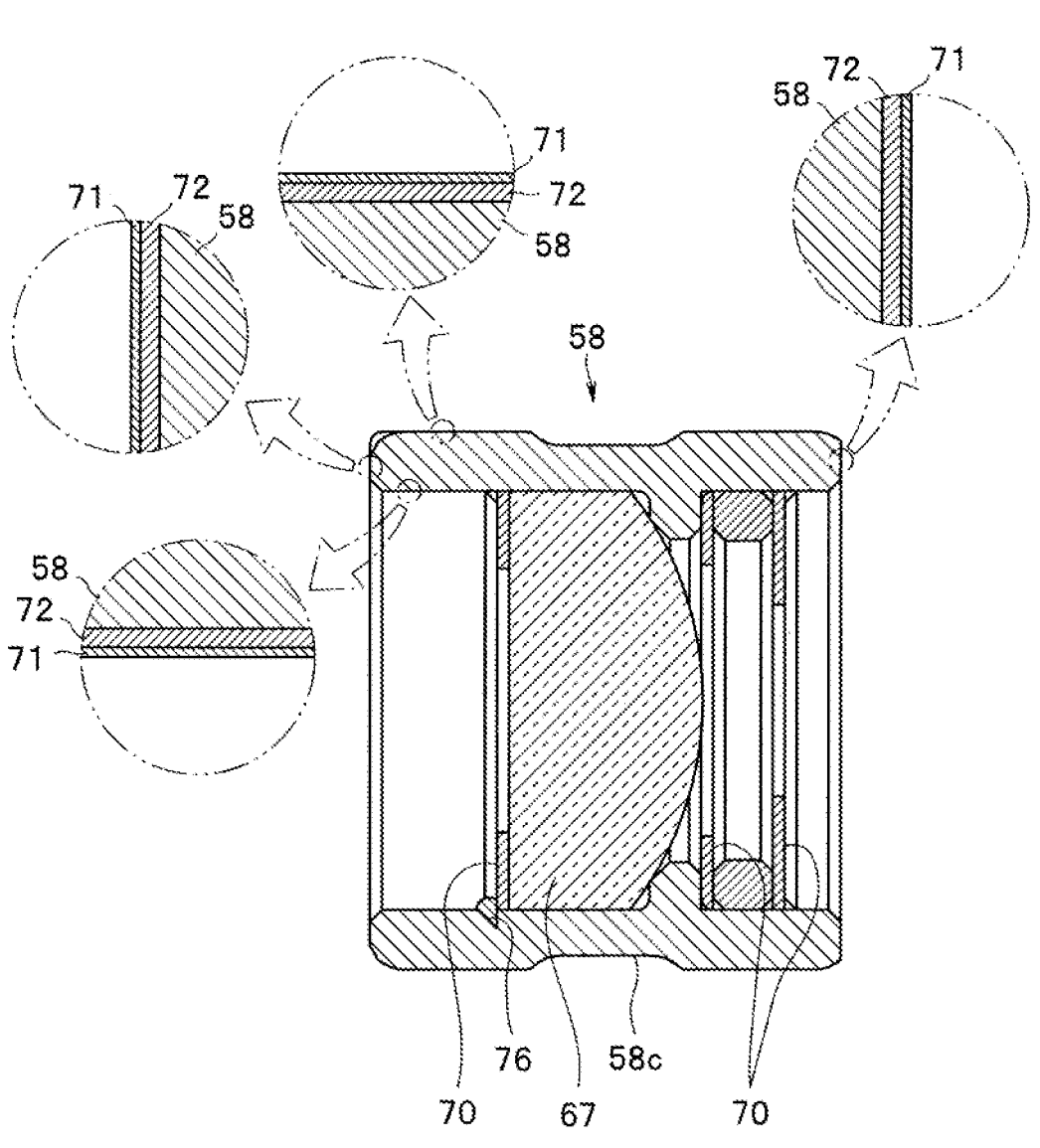
FIG. 9 relates to a second modification and is a cross-sectional view of a moving lens barrel.

As illustrated in, for example, FIG. 9, the first film 71 and the second film 72 may be formed not only on the slide surface for the coil holding barrel 57 but also on the entire surface of the moving lens barrel 58. Specifically, the first film 71 and the second film 72 may be formed on end faces and an inner peripheral surface of the moving lens barrel 58. Accordingly, deposition of the first film 71 and the second film 72 on the moving lens barrel 58 having an extremely small size can be achieved through a simple process without using a mask or the like.

The first film 71 and the second film 72 are formed on the end faces of the moving lens barrel 58, and thus when a distal end surface or a proximal end surface of the moving lens barrel 58 collides with an inner surface of the inward flange 57*i* of the coil holding barrel 57 or a distal end surface of the rear group lens barrel 56 at movement of the moving lens barrel 58, it is possible to prevent oxidation (degradation) of the surfaces. Note that, from the same viewpoint, a first film and a second film may be formed on the inner surface of the inward flange 57*i* of the coil holding barrel 57 and the distal end surface of the rear group lens barrel 56, which are surfaces contacting the moving lens barrel 58, although not illustrated.

When the first film 71 (and the second film 72) is formed on an inner surface of the moving lens barrel 58, in particular, light shielding members 70 are preferably provided on the distal end side and the proximal end side of the movable group lens 67. With the provision of the light shielding members 70, light scattered by the first film 71 can be prevented from being incident on the movable group lens 67.

When the first film 71 (and the second film 72) is formed on the inner surface of the moving lens barrel 58, a cutout part 76 for holding a bonding agent or the like for fixing the movable group lens 67 and the light shielding members 70 is preferably provided at part of the inner peripheral surface of the moving lens barrel 58 based on consideration of decrease in bonding performance of the bonding agent or the like.

Figure 10:
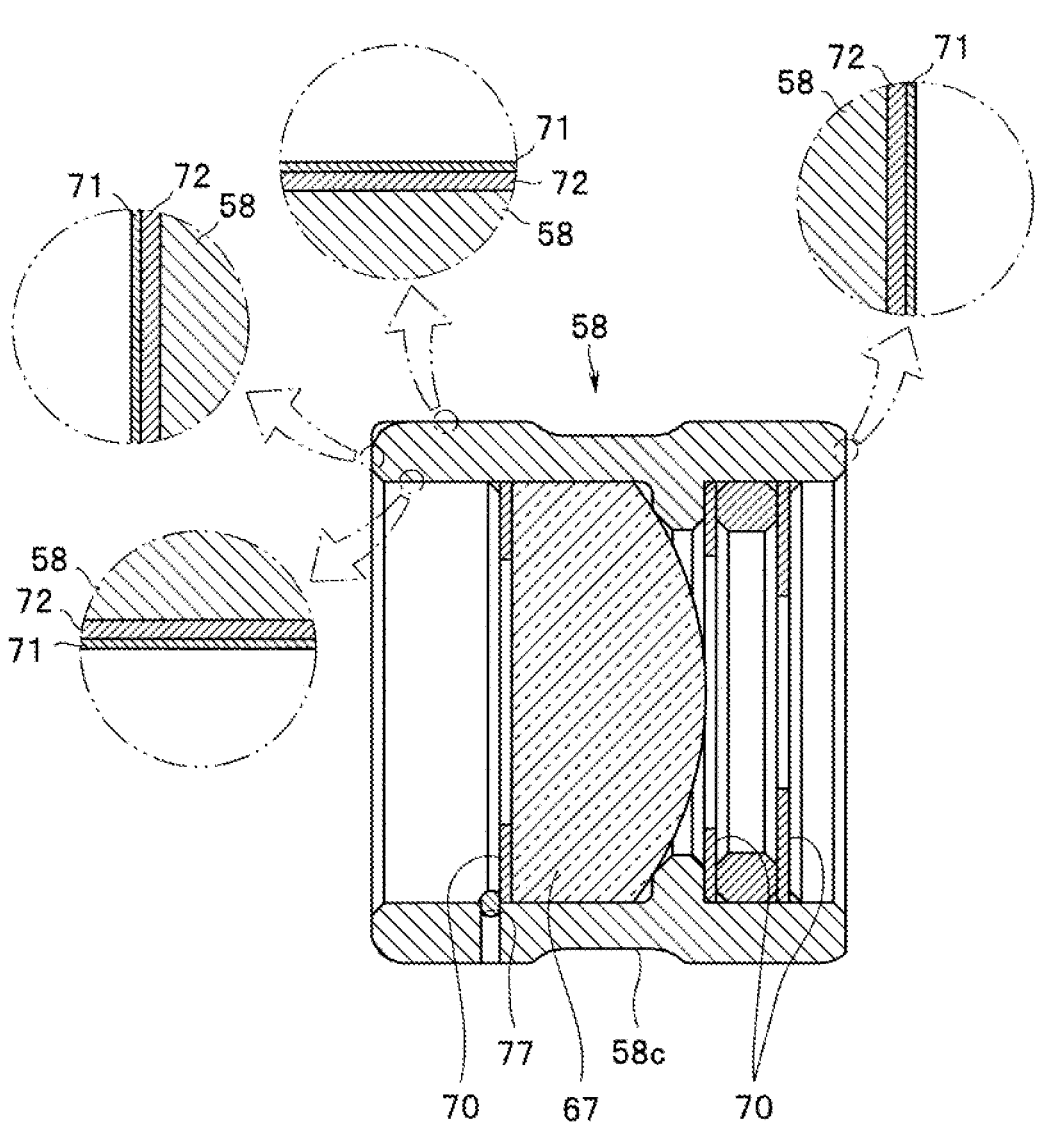
FIG. 10 relates to a third modification and is a cross-sectional view of a moving lens barrel.

Alternatively, as illustrated in, for example, FIG. 10, a through-hole penetrating through the inner peripheral surface and the outer peripheral surface of the moving lens barrel 58 may be provided in place of the cutout part 76.

Figure 11:
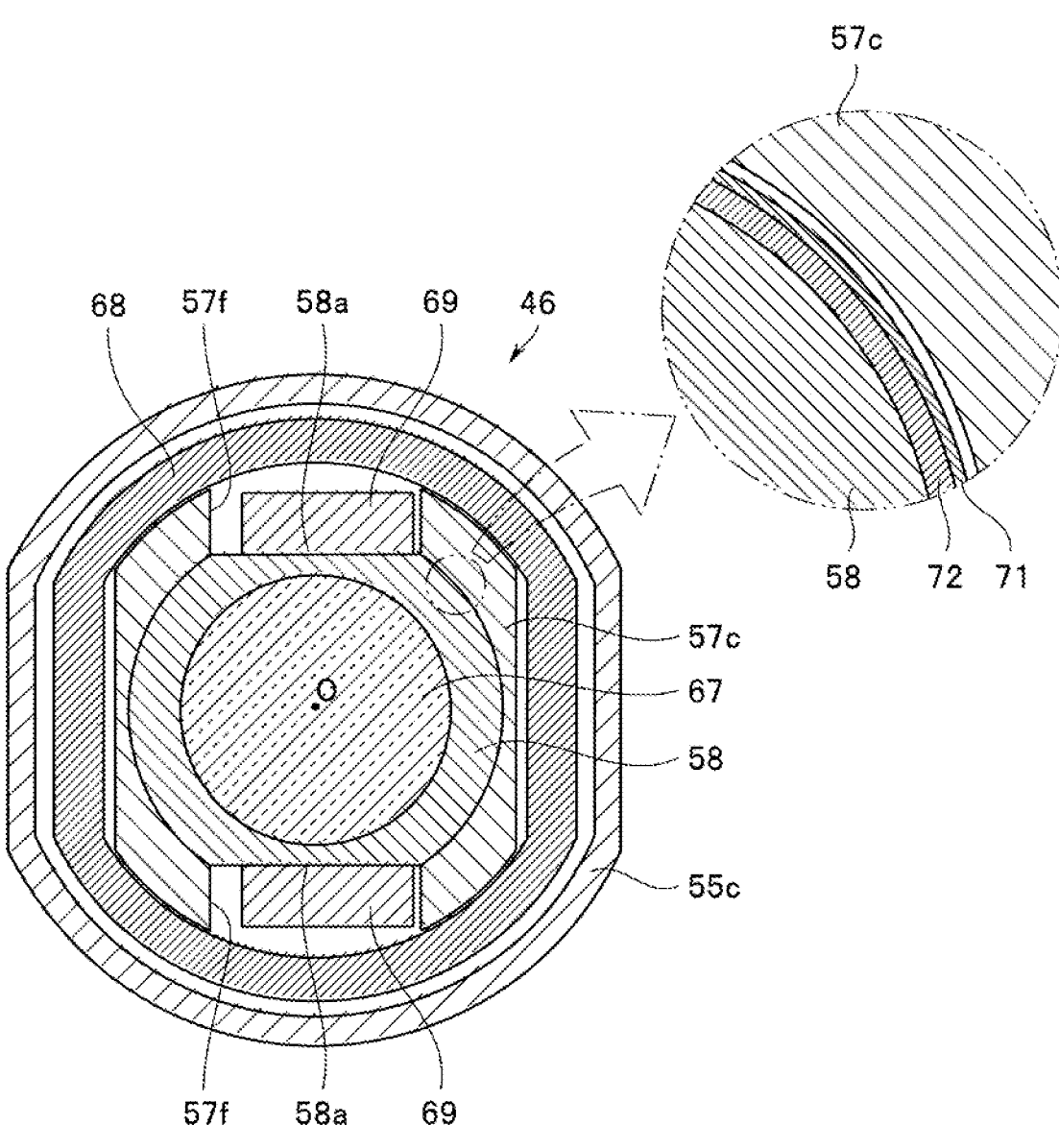
FIG. 11 relates to a fourth modification and is a cross-sectional view of an optical unit.

The above embodiment is described with an example in which the first film 71 and the second film 72 are provided on the outer peripheral surface of the moving lens barrel 58 as the slide surface for the coil holding barrel 57 and the first film 73 and the second film 74 are provided on the inner peripheral surface of the coil holding barrel 57 (inner peripheral surfaces of the distal-end-side barrel part 57*c* and the intermediate barrel part 57*d*) as the slide surface for the moving lens barrel 58, but the present invention is not limited to the example. Specifically, as illustrated in, for example, FIG. 11, the first film 71 and the second film 72 may be provided on the outer peripheral surface of the moving lens barrel 58 as the slide surface for the coil holding barrel 57, and the first film 73 and the second film 74 may be omitted from the inner peripheral surface of the coil holding barrel 57 (inner peripheral surfaces of the distal-end-side barrel part 57*c* and the intermediate barrel part 57*d*) as the slide surface for the moving lens barrel 58.

Figure 12:
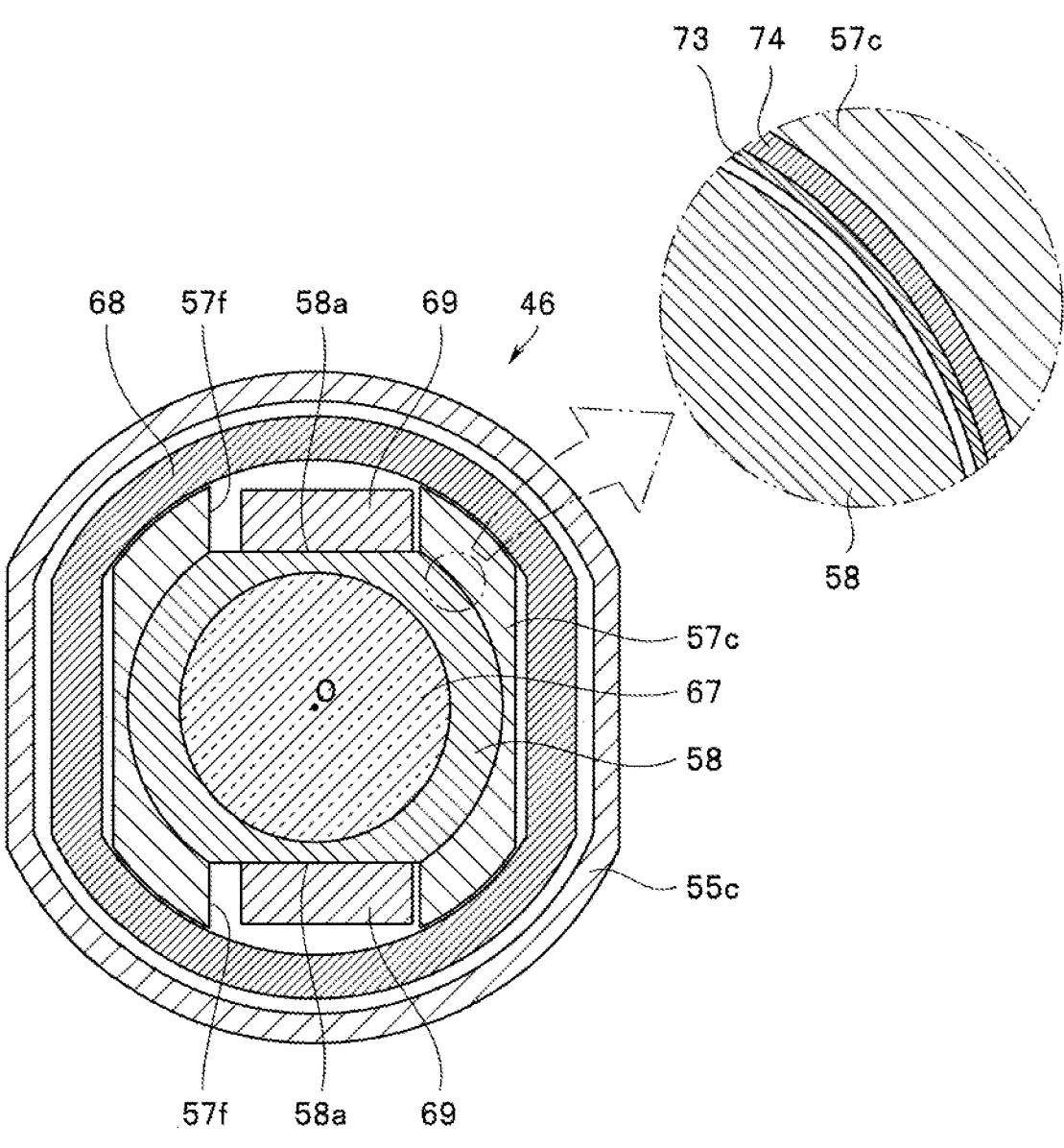
FIG. 12 relates to a fifth modification and is a cross-sectional view of an optical unit.

Alternatively, as illustrated in, for example, FIG. 12, the first film 71 and the second film 72 may be omitted from the outer peripheral surface of the moving lens barrel 58 as the slide surface for the coil holding barrel 57, and the first film 73 and the second film 74 may be provided on the inner peripheral surface of the coil holding barrel 57 (inner peripheral surfaces of the distal-end-side barrel part 57*c* and the intermediate barrel part 57*d*) as the slide surface for the moving lens barrel 58.

The above embodiment is described with an example in which the moving lens barrel 58 is made of SUS303 or the like, but the moving lens barrel 58 may be made of a material having magnetism (magnetic material), for example. With this configuration, the moving lens barrel 58 can be exploited as a yoke to improve magnetic force of the magnets 69. Thus, it is possible to further downsize the magnets 69 and more effectively downsize the objective optical unit 46.

Note that the present invention is not limited to the above-described embodiment but may be provided with modifications and changes in various kinds of manners, which are included in the technical scope of the present invention.

What is claimed is:

1. An optical unit comprising:

an observation optical system including a fixed lens and a moving lens;

a fixed barrel holding the fixed lens;

a movable barrel disposed in the fixed barrel, holding the moving lens, and configured to move in a direction along a photographing optical axis of the observation optical system;

a first film formed on at least one of slide surfaces of the fixed barrel and the movable barrel that slide relative to each other, the first film serving as an oxidation reaction prevention layer configured to prevent corrosion of the slide surface;

a second film interposed between the slide surface on which the first film is formed and the first film, the second film serving as a stress reduction layer configured to prevent crack of the first film; and a voice coil motor configured to relatively move the movable barrel with respect to the fixed barrel in the optical axis direction by using a coil disposed at the fixed barrel and a magnet disposed at the movable barrel, wherein the first film and the second film are formed on both of the slide surfaces of the movable barrel and the fixed barrel, and wherein the first film and the second film are formed on a surface of a cutout part surrounding the magnet disposed in the movable barrel.

2. The optical unit according to claim 1, wherein the first film contains a noble metal component.

3. The optical unit according to claim 2, wherein the first film contains a component of any of gold, palladium, and platinum, the component having a high corrosion resistance.

4. The optical unit according to claim 1, wherein the second film is made of a material having a substantially same Young's modulus as a material of the fixed barrel or the movable barrel.

5. The optical unit according to claim 1, wherein the second film contains at least a Ni component.

6. The optical unit according to claim 1, wherein the first film is made of a material having a substantially same linear expansion coefficient as a material of the second film.

7. The optical unit according to claim 1, wherein the first film and the second film are formed on a surface of the fixed barrel or the movable barrel.

8. The optical unit according to claim 1, wherein the first film is thinner than the second film.

9. The optical unit according to claim 1, wherein the second film is at least twice thicker than the first film.

10. The optical unit according to claim 1, wherein the movable barrel has a recessed part that collects a small amount of powder dust generated on the slide surface.

11. The optical unit according to claim 1, further comprising a light shielding member that is provided at the movable barrel and configured to shield light scattered by the first film before and after the moving lens in the direction along the photographing optical axis of the observation optical system.

12. The optical unit according to claim 1, wherein the movable barrel is configured to contact at a distal end and a proximal end within the fixed barrel, and the first film and the second film are formed at contact portions.

13. The optical unit according to claim 1, wherein the fixed barrel is provided with the first film and the second film on a surface contacting the movable barrel.

14. The optical unit according to claim 1, further comprising a cutout part formed by partially cutting out at least one of an inner peripheral surface of the fixed barrel or the slide surface of the fixed barrel in an axis orthogonal direction of an optical axis of the fixed barrel.

15. The optical unit according to claim 1, wherein the movable barrel is made of a magnetic material.

16. The optical unit according to claim 1, wherein the movable barrel is attracted to and held at a predetermined position of the fixed barrel at energization of the voice coil motor, and the movable barrel is movable in the fixed barrel at non-energization of the voice coil motor.

17. An image pickup unit comprising:

an optical unit; and an image pickup device unit disposed on an optical axis of the optical unit, wherein the optical unit includes: an observation optical system including a fixed lens and a moving lens; a fixed barrel holding the fixed lens; a movable barrel disposed in the fixed barrel, holding the moving lens, and configured to move in a direction along a photographing optical axis of the observation optical system; a first film formed on at least one of slide surfaces of the fixed barrel and the movable barrel that slide relative to each other, the first film serving as an oxidation reaction prevention layer configured to prevent corrosion of the slide surface; a second film interposed between the slide surface on which the first film is formed and the first film, the second film serving as a stress reduction layer configured to prevent crack of the first film; and a voice coil motor configured to relatively move the movable barrel with respect to the fixed barrel in the optical axis direction by using a coil disposed at the fixed barrel and a magnet disposed at the movable barrel, wherein the first film and the second film are formed on both of the slide surfaces of the movable barrel and the fixed barrel, and wherein the first film and the second film are formed on a surface of a cutout part surrounding the magnet disposed in the movable barrel.

18. An endoscope comprising an optical unit at a distal end portion of an insertion portion configured to be inserted into a subject, wherein the optical unit includes: an observation optical system including a fixed lens and a moving lens; a fixed barrel holding the fixed lens; a movable barrel disposed in the fixed barrel, holding the moving lens, and configured to move in a direction along a photographing optical axis of the observation optical system; a first film formed on at least one of slide surfaces of the fixed barrel and the movable barrel that slide relative to each other, the first film serving as an oxidation reaction prevention layer configured to prevent corrosion of the slide surface; a second film interposed between the slide surface on which the first film is formed and the first film, the second film serving as a stress reduction layer configured to prevent crack of the first film; and a voice coil motor configured to relatively move the movable barrel with respect to the fixed barrel in the optical axis direction by using a coil disposed at the fixed barrel and a magnet disposed at the movable barrel, wherein the first film and the second film are formed on both of the slide surfaces of the movable barrel and the fixed barrel, and wherein the first film and the second film are formed on a surface of a cutout part surrounding the magnet disposed in the movable barrel.

* * * * *